United States Patent [19]
Levy

[11] Patent Number: 5,337,896
[45] Date of Patent: Aug. 16, 1994

[54] SPECIMEN PACKAGE

[76] Inventor: Abner Levy, 325 N. Oakhurst Dr., P4, Beverly Hills, Calif. 90210

[21] Appl. No.: 984,903

[22] Filed: Dec. 2, 1992

Related U.S. Application Data

[63] Continuation-in-part of Ser. No. 706,890, May 29, 1991, Pat. No. 5,176,257, which is a continuation-in-part of Ser. No. 552,332, Jul. 13, 1990, Pat. No. 5,050,735.

[51] Int. Cl.$^5$ ............................................. B65D 85/48
[52] U.S. Cl. ................................... 206/456; 206/478; 206/482
[58] Field of Search .................... 206/449-456, 206/472, 477, 478, 482; 279/92.1, 92.3, 92.7, 92.8

[56] References Cited

U.S. PATENT DOCUMENTS

| | | | |
|---|---|---|---|
| 936,777 | 10/1909 | Herzfelder | 206/482 |
| 1,141,172 | 6/1915 | Clark | 229/92.8 |
| 1,577,043 | 3/1926 | Mackey | 229/92.8 |
| 1,643,421 | 9/1927 | Rowar | 206/482 |
| 2,147,470 | 2/1939 | Tate | 206/482 X |
| 2,198,138 | 4/1940 | Sutton | 206/482 |
| 2,298,601 | 10/1942 | Tremblett | 229/92.7 |
| 2,985,288 | 5/1961 | Reich | 206/363 |
| 4,078,656 | 3/1978 | Crane et al. | 206/456 X |
| 5,050,735 | 9/1991 | Levy | 206/456 |
| 5,176,257 | 1/1993 | Levy | 206/456 |

FOREIGN PATENT DOCUMENTS 102650  12/1916  United Kingdom ............... 229/92.8

Primary Examiner—Bryon P. Gehman
Attorney, Agent, or Firm—Beehler & Pavitt

[57] ABSTRACT

A package for a medical specimen slide formed by a sheet foldable to a packaged condition has end panels and side panels joined to a central base portion of the sheet, each end panel having corner portions foldable to a crush resistant configuration so as to support the end panels and the side panels away from contact with the specimen slide. The package sheet also has a slide retainer consisting of two cuts in the sheet spaced to define a retaining band under which is inserted the specimen slide for retention to the package sheet.

25 Claims, 8 Drawing Sheets

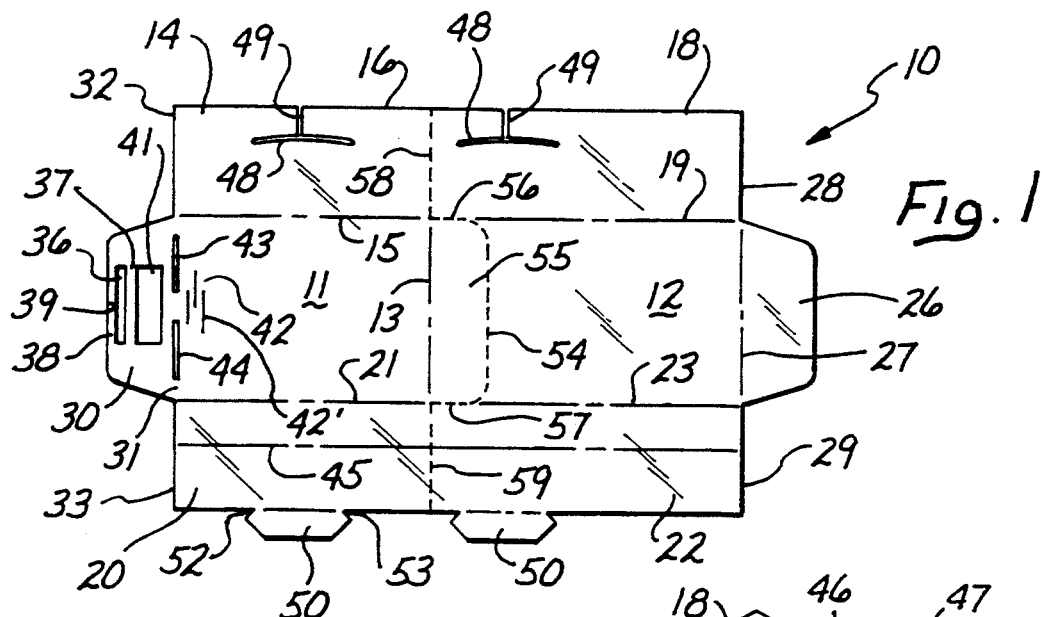
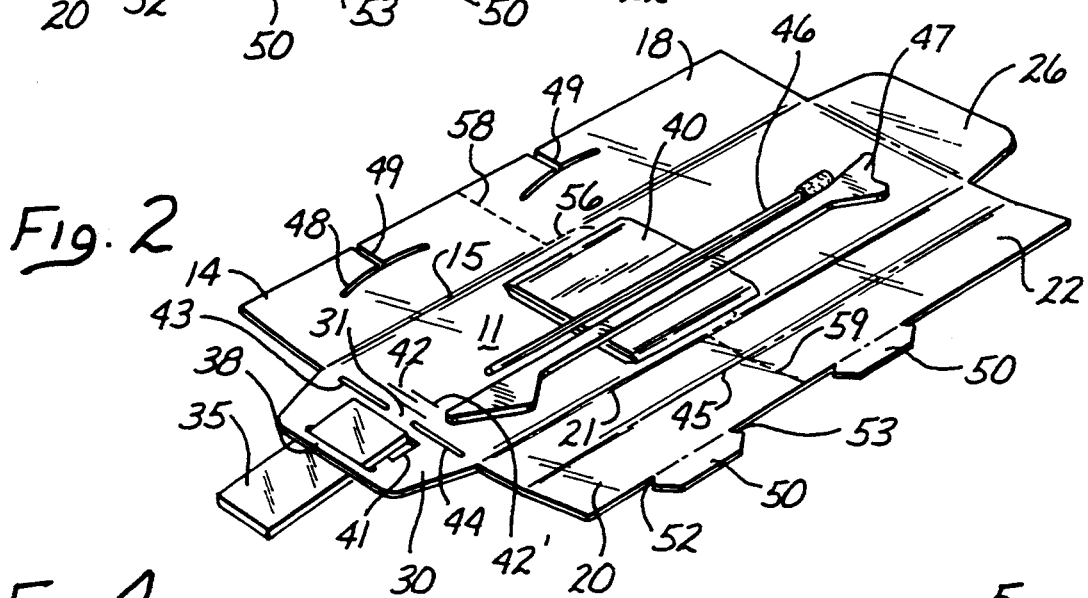
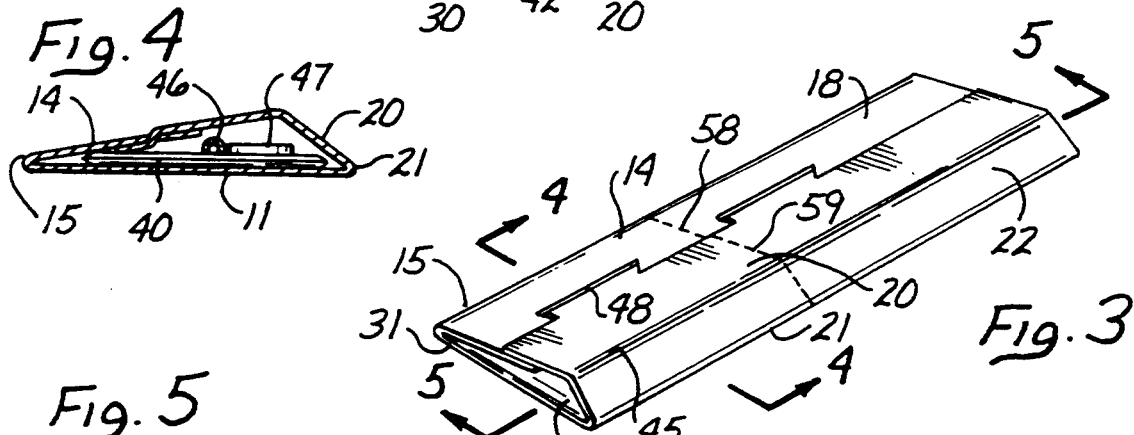
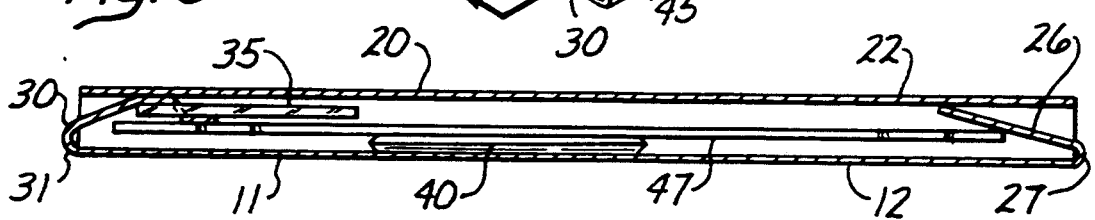

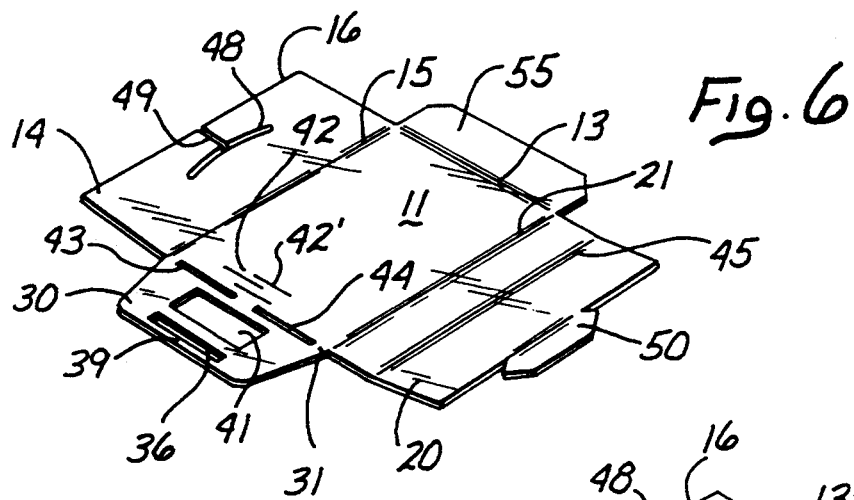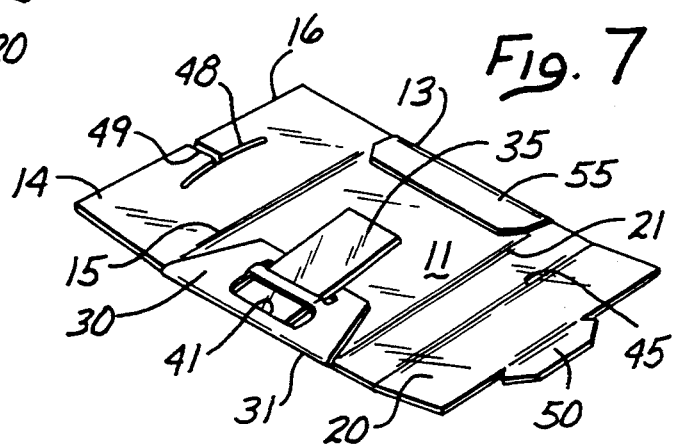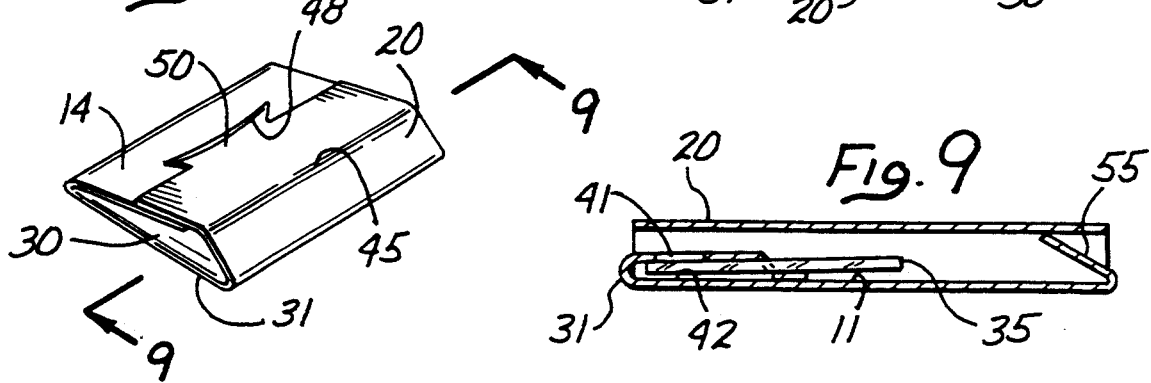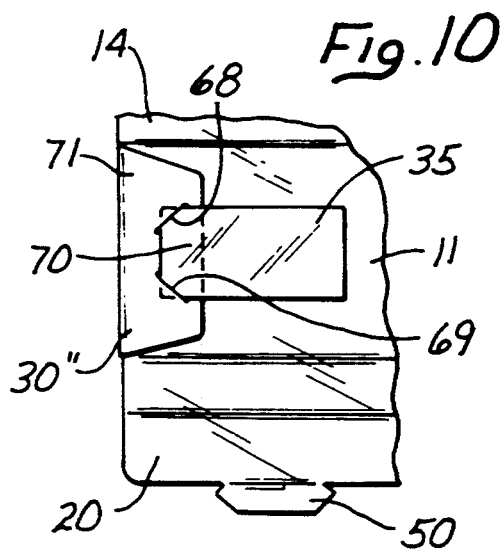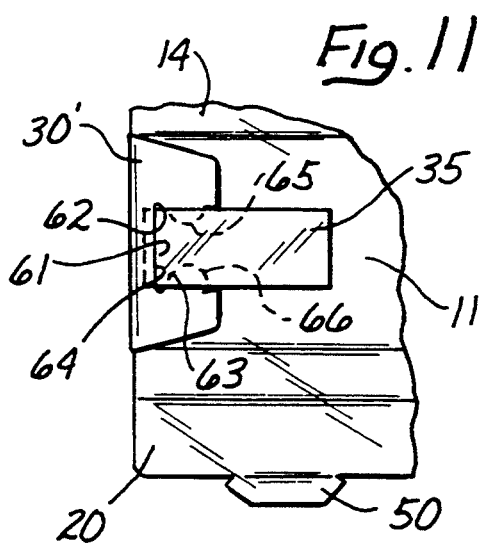

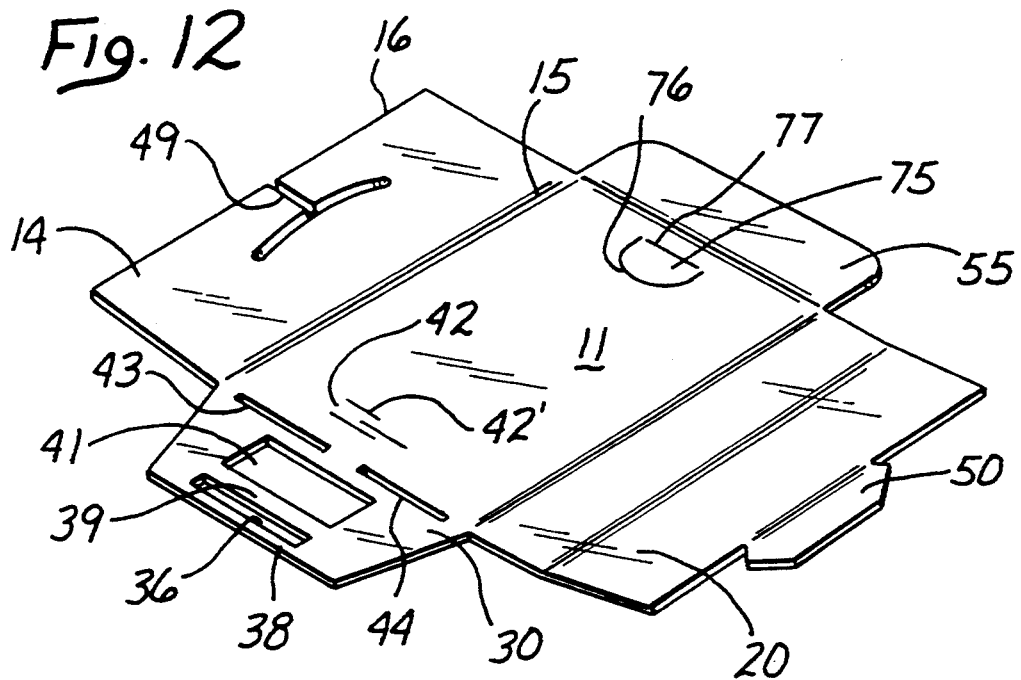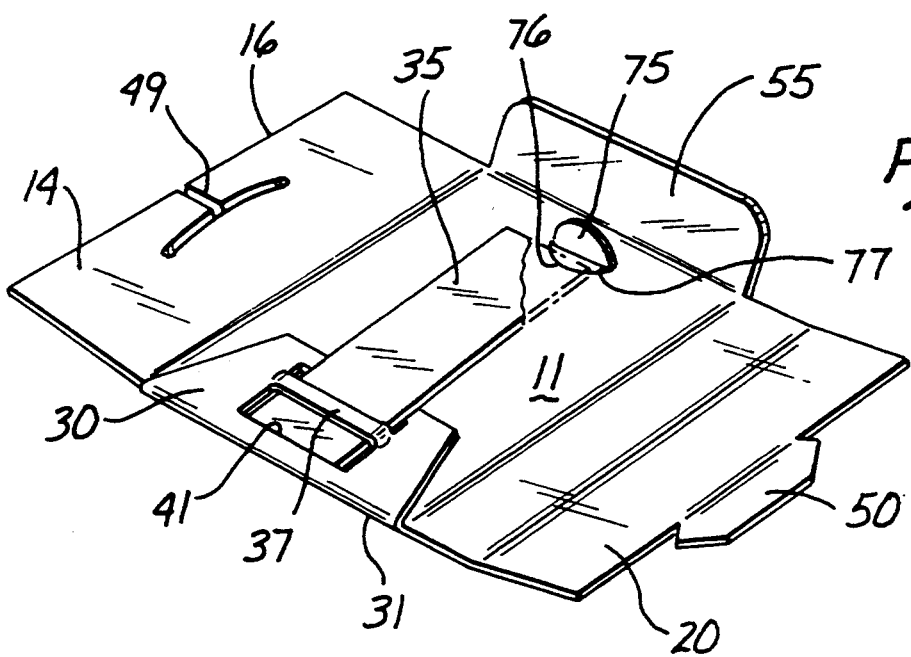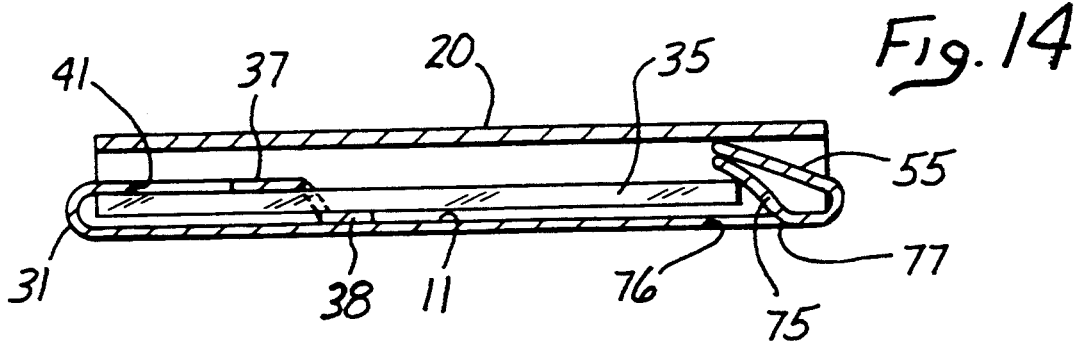

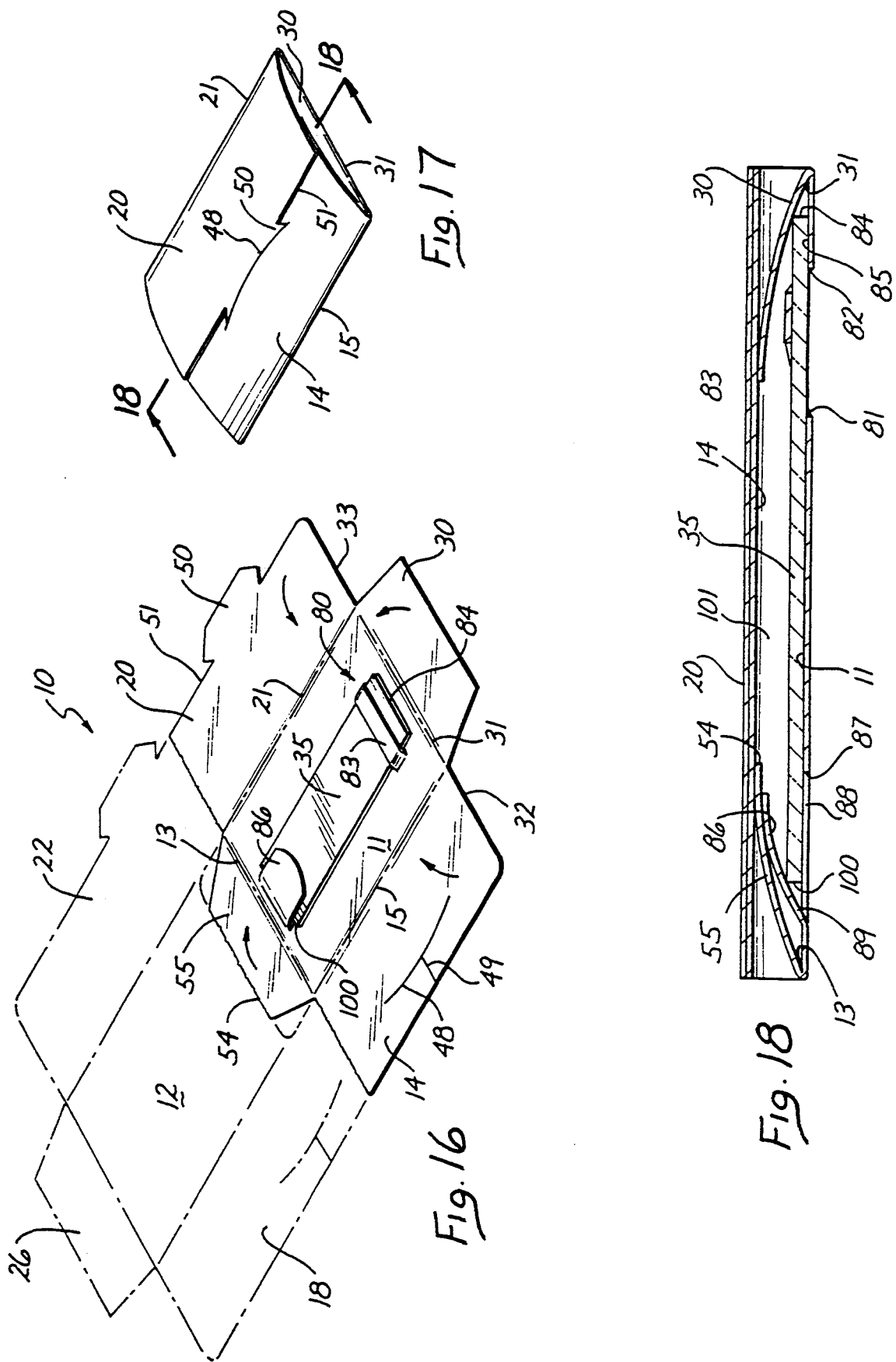

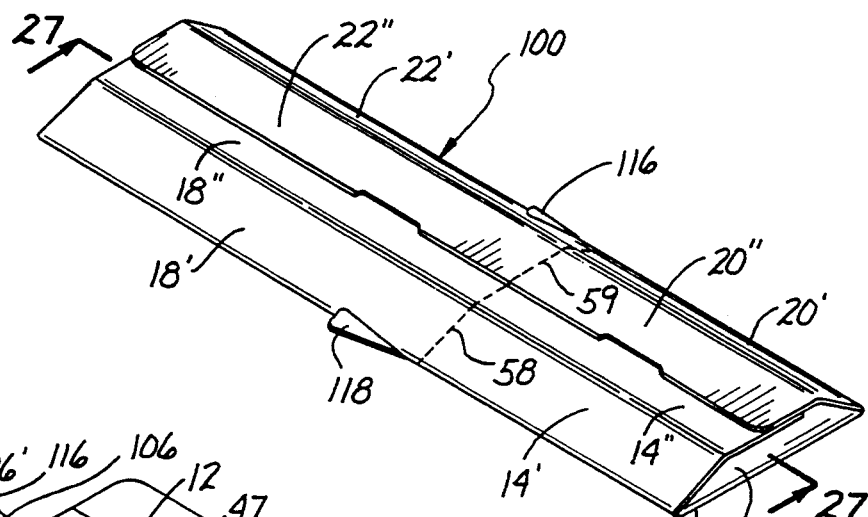
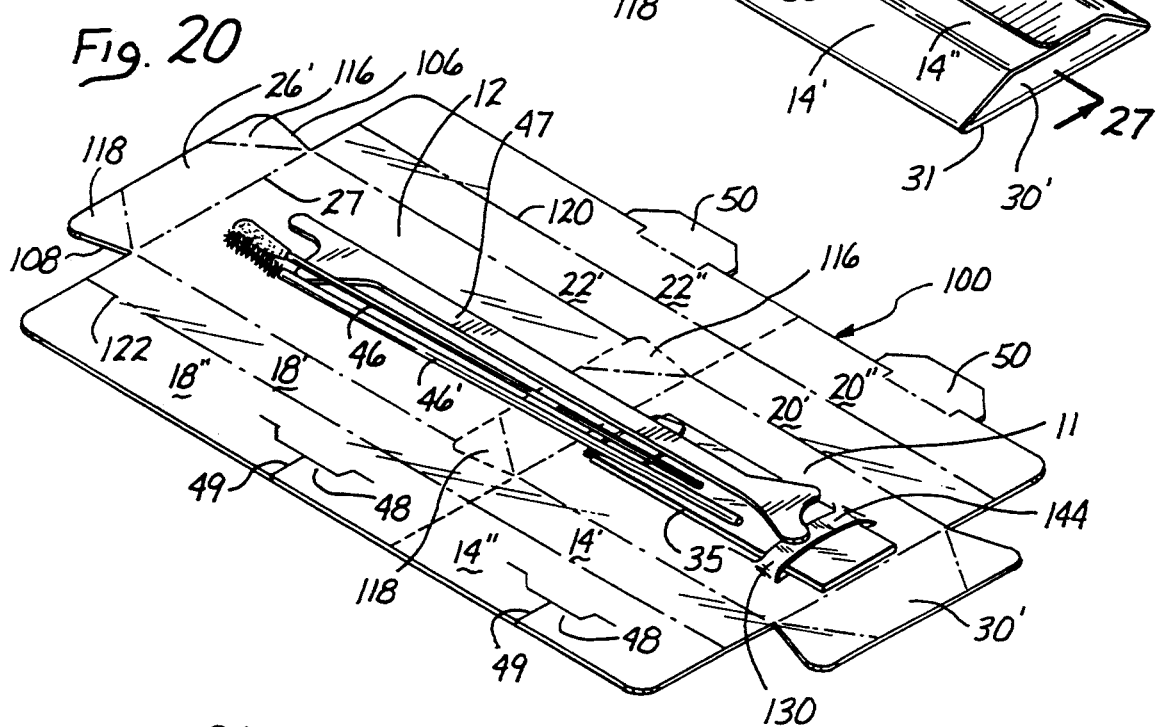
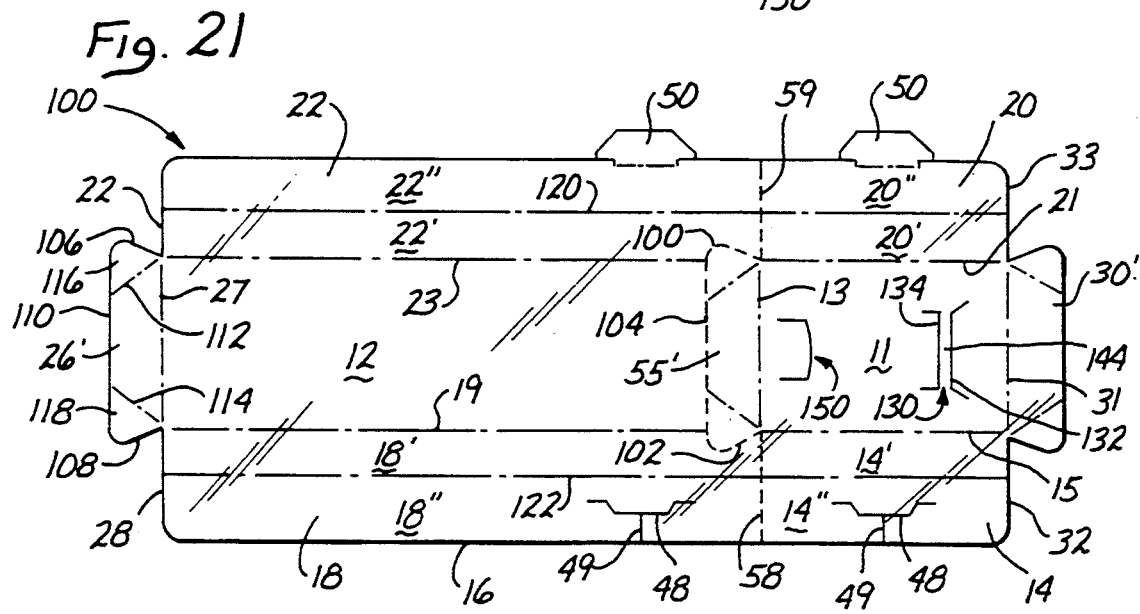

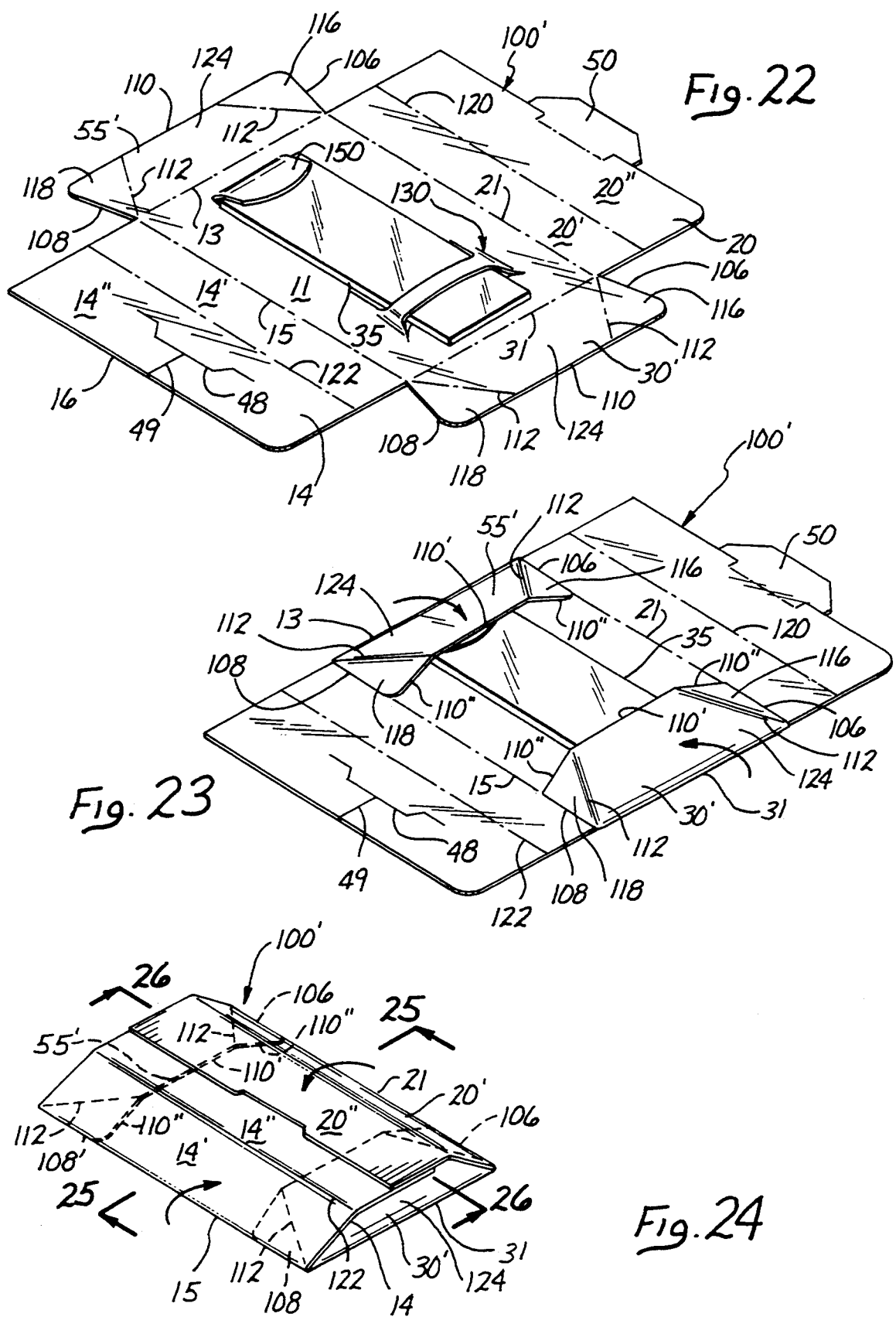

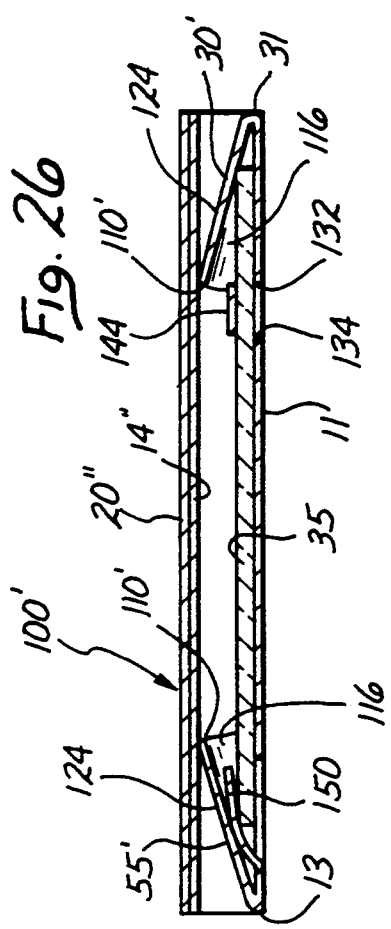
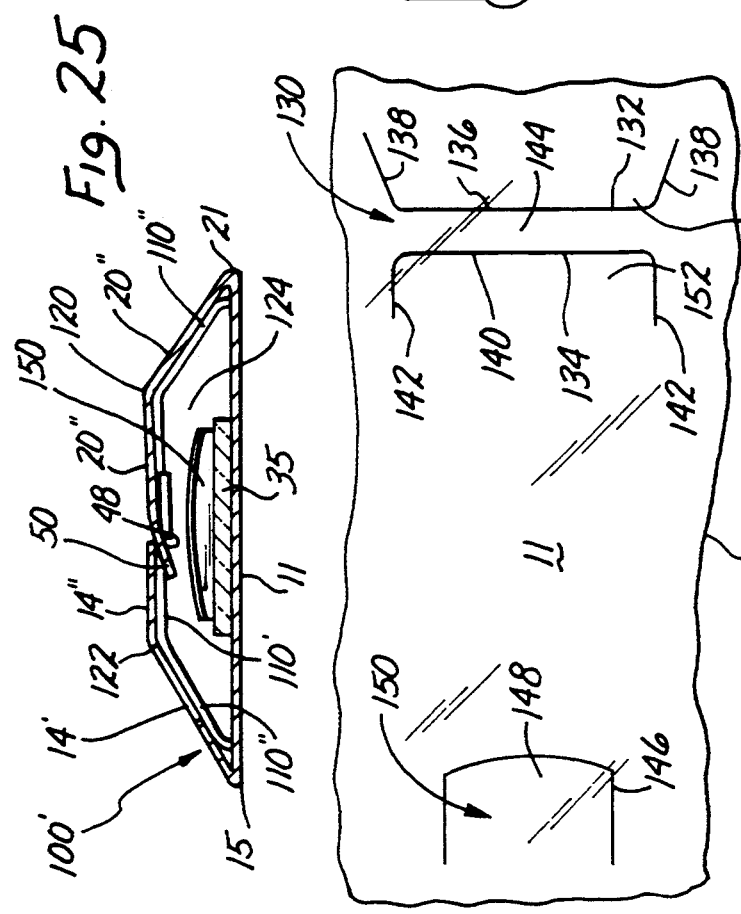
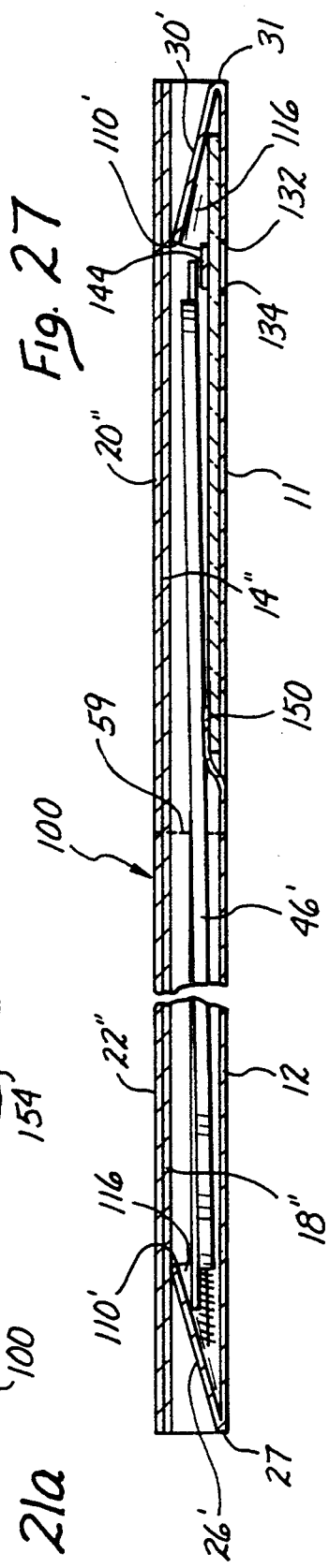

SPECIMEN PACKAGE

This is a continuation-in-part of application Ser. No. 07/706,890, filed May 29, 1991, now U.S. Pat. No. 5,176,257, which is a continuation-in-part of application Ser. No. 07/552,332, filed Jul. 13, 1990, now issued as U.S. Pat. No. 5,050,735.

For the handling of specimens for laboratory analysis in the medical and related fields, current practice is to have as much of the necessary paraphernalia as possible of a disposable character. Although biological and medical specimens in the final stage ready for microscopic or other examination may be compact and require little space for preservation and handling, that circumstance may not prevail during preparation for and collection of the specimen. This is to say that for the collection of a specimen, the technician frequently has need for instruments, swabs, disinfectants, patches and the like, necessary for requiring the needed scraping, tissue or fluid accumulation which, once having been used, is no longer needed and can be disposed of.

Conversely, the specimen itself whether one for microscopic examination or chemical analysis, need only be very small, needs only modest means for preservation and requires a correspondingly small package in which to preserve it and deliver it for analysis.

It is therefore among the objects of the invention to provide a new and improved reusable-type package for acquisition and retention of a specimen, parts of which are readily disposable when no longer needed.

Another object of the invention is to provide a new and improved reusable package for the acquisition and retention of a specimen, which features a relatively larger package in which all necessary paraphernalia needed for acquisition of the specimen can be carried, but which is separable so as to leave only a relatively smaller package for the finally acquired specimen, by means of which it can be delivered to a laboratory for analysis.

Another object of the invention is to provide a new and improved reusable-type specimen package wherein an effective mounting for a specimen slide is provided in such manner that it is handily located and well protected during both the collecting stage as well as the final use stage and which is accompanied by adequate and readily available means for identification.

Still another object of the invention is to provide a new and improved reusable-type specimen package which is compact when filled with the necessary paraphernalia, and further which is of such character that it can be divided into a smaller compact package for containing only the specimen, permitting the surplus packaging to be disposed of.

Still further among the objects of the invention is to provide a new and improved reusable-type specimen package of adequate proportions to contain collection of paraphernalia and the final specimen, which is easily and readily manipulatable during collection and final disposition, relatively inexpensive and readily disposable as to those portions which may no longer be needed once the specimen has been collected and ready for delivery to the laboratory.

With these and other objects in view, the invention consists of the construction, arrangement and combination of the various parts of the device serving as examples only of one or more embodiments of the invention, whereby the objects contemplated are attained, as hereinafter disclosed in the specification and drawings, and pointed out in the appended claims.

In the Drawings:

FIG. 1 is a plan view of the sheet of material cut to shape and size for the package.

FIG. 2 is a perspective view of the sheet of material equipped for initial packaging.

FIG. 3 is a perspective view of the initially formed package.

FIG. 4 is a cross-sectional view on the line 4—4 of FIG. 3.

FIG. 5 is a longitudinal sectional view on the line 5—5 of FIG. 3.

FIG. 6 is a perspective view of that portion of the sheet of material used for the final package.

FIG. 7 is a view similar to FIG. 6, but partly folded over for packaging.

FIG. 8 is a perspective view of a completed final package.

FIG. 9 is a longitudinal sectional view on the line 9—9 of FIG. 8.

FIG. 10 is a fragmentary plan view of a second form of the sheet of material as equipped for packaging.

FIG. 11 is a fragmentary plan view of a third form of the sheet of material as equipped for packaging.

FIG. 12 is a perspective view of that portion of the sheet of material used for the final package of a modified form of the device.

FIG. 13 is a perspective view similar to FIG. 12 wherein the slide is shown in place.

FIG. 14 is a cross-sectional view of the final package of the modified form of FIGS. 12 and 13.

FIG. 16 is a view as in FIG. 15, showing in solid lining that portion of the sheet used for the final package, the portion of the sheet shown in phantom lining being separated for packaging the specimen strip;

FIG. 17 is a perspective view of the solid lined portion of the sheet of FIG. 16 folded to its packaged position; and FIG. 18 is a cross section taken along line 18—18 in FIG. 17.

FIG. 19 is a perspective view of a third embodiment of the specimen package shown in original packaged condition;

FIG. 20 shows the package of FIG. 19 laid open to show the specimen slide mounted to the slide retainers and the specimen collection implements placed on the package sheet;

Figure 15:
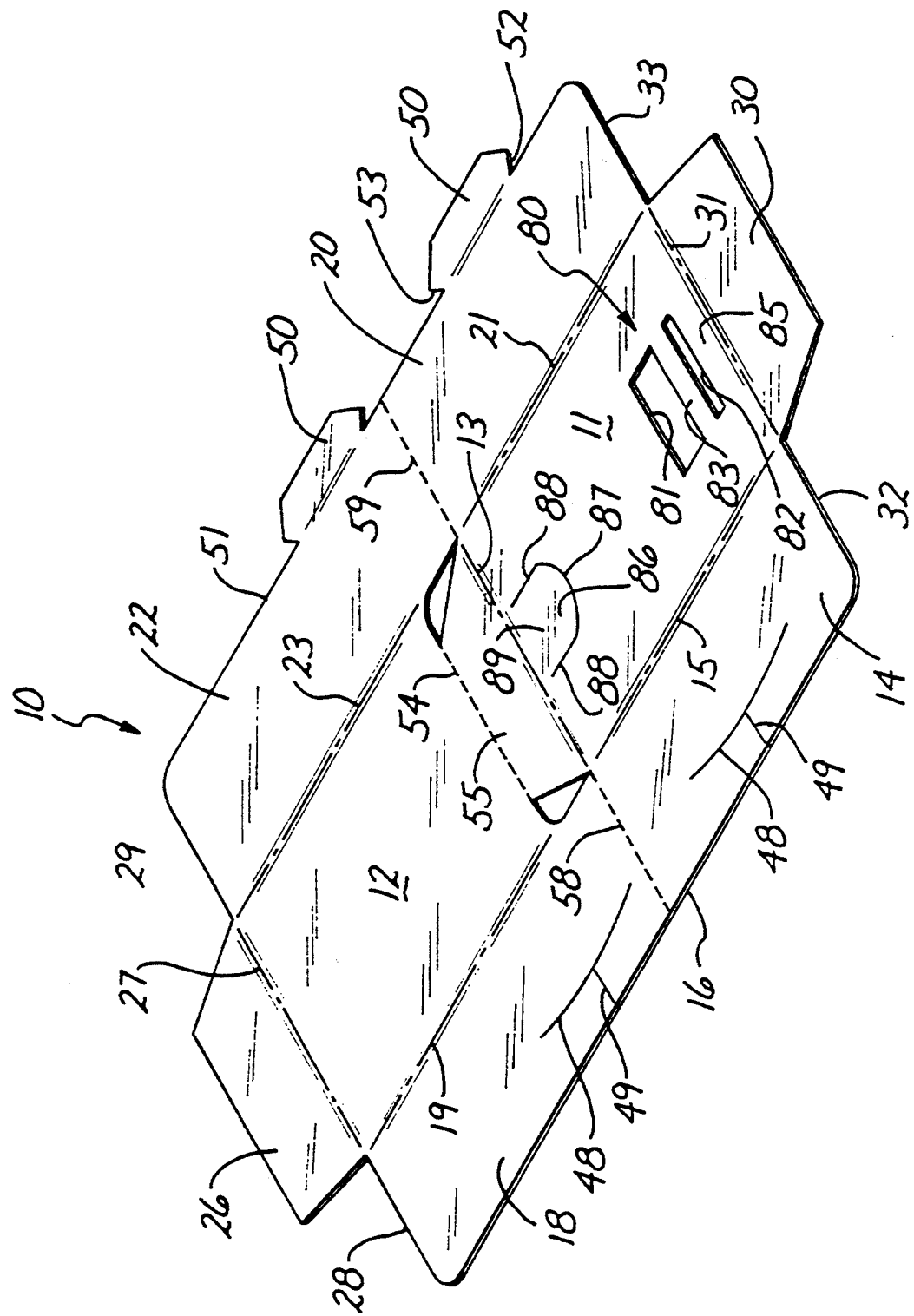
FIG. 15 is a perspective view of a fourth form of the sheet of material used to package the specimen strip.

FIG. 21 and 21c each show a top plan view of the package sheet of FIG. 20 laid open;

FIG. 22 is a perspective view of the slide carrying portion of the package sheet detached from the original package sheet of FIGS. 19 through 21;

FIG. 23 is a perspective view of the detached sheet portion of FIG. 22, showing the end panels folded towards the packaged condition of the detached sheet portion;

FIG. 24 shows the sheet portion of FIG. 23 fully folded to its finally packaged condition for conveying a medical specimen on the slide in the package;

FIG. 25 is a cross sectional view taken along line 25—25 in FIG. 24, showing the medical slide mounted in the final package;

FIG. 26 is a longitudinal cross section of the package of FIG. 24 taken along line 26—26;

FIG. 27 is a longitudinal view of the original specimen collection kit package taken along line 27—27 in FIG. 19;

In an embodiment of the invention chosen for the purpose of illustration there is shown a sheet of packaging material for assembly into a specimen package indicated generally by the reference character 10, which consists essentially of a single sheet of package material specially cut for folding in a distinctive fashion. The package is made up of two central base portions 11 and 12 separated by a transverse fold line 13. The two base portions together form, in effect, a long rectangular bottom for the package in its initial form. On one side of the base portion 11 is a side panel 14 with a captive side edge joined by a fold line 15 to a corresponding side edge of the base panel 11, leaving a free edge 16.

Similarly, for the base portion 12 there is a side panel 18 with a captive side edge joined by a fold line 19 to a corresponding side edge of the base portion 12. The fold lines 15 and 19 are continuous with respect to each other forming one fold line for the combined side panels 14 and 18 permitting them to be folded over the initially joined base portions 11 and 12.

On the opposite side of the base portion 11 is a side panel 20 having a captive edge joined to a corresponding edge of the base portion 11 along a fold line 21. Again, for the base portion 12 there is a side panel 22 joined along a fold line 23 to a corresponding edge of the base portion 12. It is of consequence to note in this connection that the combined width of the side panels 14 and 20 is materially greater than the width of the corresponding base portion 11. Similarly, the combined width of the side panels 18 and 22 is materially greater than the width of the base panel 12.

At the free end of the base portion 12 is an end panel 26 joined at its captive edge to a corresponding edge of the base along a fold line 27. The fold line 27 is in alignment with an end edge 28 of the side panel 18 and a similar end edge 29 of 22 the side panel 22.

At the opposite end of the package there is another end panel 30 joined at its captive edge to a corresponding edge of the base portion 11 along a fold line 31. The fold line 31 is in alignment with an end edge 32 of the side panel 14 and a corresponding end edge 33 of the side panel 20.

One of the end panels, namely, the end panel 30 as shown, provides for attachment of a specimen strip 35, a specimen strip customarily being a transparent glass or plastic strip for reception of the physical specimen for which analysis is sought. As shown in the form of invention of FIG. 1, the end panel 30 is provided with a slot 36 long enough to accommodate the width of the specimen strip and wide enough to comfortably accommodate the thickness.

In the embodiment shown there is a bar 37 forming one side of the slot 36 and a second bar 38 forming the other side, the bar 38 being separated by a slit 39. At the relative mid-portion of the end panel 30 there is provided a window 41. The window has a length approximately equal to the length of the slot 36 and a width substantially greater. Beneath the window is a space 42 which is provided for identification of the specimen which is to be collected on the specimen strip 35.

By providing retention means on the end panel 30 for the specimen strip 35 in the form and manner described, the specimen strip can be attached to the end panel when the panel is in open position, and then the tab with the strip swung over the corresponding face of the bottom portion 11. Insertion and removal of the strip can also take place when the end panel is folded over. By having the specimen strip capable of being lifted with the end panel, there is ready access to the space 42 for specimen identification insignia 42', after which it is covered over by replacement of the strip and end panel.

It is additionally noteworthy to have cuts 43 and 44 extending partway along the length of the fold line 31. With the fold line cut in this fashion, the end panel and connected specimen strip can be more readily compacted in final position during the packaging. There is a comparable advantage in the provision of a score line 45 operable when the initial package is closed. The end panel 30 with a single window 41 is by way of example only. On occasion two windows each with a strip may be preferred. The side panels 14 and 20 also provide package material where windows and strip may be located, if desired, assisted if need be with cuts like the cuts 43 and 44 which assist the end panel 30.

For closing and holding the package in closed position, the side panel 14 is provided with a slightly arcuate slit 48, with an escape slit 49 extending to the free edge 16. There is a comparable slit and escape slit for the side panel 18. On the opposite side of the base portion 11, the side panel 20 is provided with a flap 50 on a corresponding free edge 51. The side panel 20 has notches 52 and 53 at opposite ends of the flap 50. The notches determine an effective length for the flap as being slightly greater than the length of the slit 48 when the flap is interlocked with the slit. The side panel 22 is similarly equipped.

It has been found advantageous to have the aggregate width of the side panel 20 and the distance between the fold line 15 and the slit 48 slightly greater than the width of the base portion 11. Dimensioned as described, coupled with a slight folding at the score line 45, provides for a space beneath the side panels 14 and 20 when they are folded over each other to allow for accommodation not only of the specimen strip 35, but other paraphernalia which may be initially contained within the package such, for example, as a swab 46, tongue depressor 47 and fixative package 49.

There is additionally provided a line of perforations between the base portion 11 together with its side panels 14 and 20, and the base portion 12 together with its side panels 18 and 22. A central section 54 of the line of perforations separates the base portion 12 from an auxiliary end panel 55. Side sections 56 and 57 of the line of perforations defines side edges of the auxiliary end panel 55. A section 58 of the line perforations separates the side panels 14 and 18 and a section 59 separates side panels 20 and 22.

When the full size of the package as shown in FIG. 3 is no longer needed, the package is separated along the lines of perforations just described so that the base portion 11 with its newly acquired auxiliary end panel 55 can be made into a smaller separate package as shown in FIG. 8 completed by the presence of the folded-over side panels 14 and 20. The base portion 12, with its side panels 18 and 22 and end panel 26 being no longer needed, may be disposed of, together with such paraphernalia as may initially have been needed. Under these circumstances, the smaller of the packages which contains the specimen strip 35 and its identification is readily closeable for transportation and storage until needed.

In a second form of the invention, an end panel 30' is shown provided with a window 61 formed by side edges 62 and 63 with an end edge 64. Tabs 65 and 66 are located on corresponding side edges 62 and 63 and provide for retention of the specimen strip 35. There is abundant space beneath the window for use in identification.

In another form of the device, an end panel 30" is shown provided with diagonally disposed slits 68, 69 for retention of the specimen strip 35. A space 70 on the corresponding face of the end panel serves for use in identification of the specimen.

In the form of the device of FIGS. 12, 13 and 14, use is made of a holding tab 75 for additional retention of the otherwise free end of the specimen strip 35. The holding tab shown by way of example is cut from the base portion 11 along an arcuate line 76. A folding line 77 of the holding tab is at a location adjacent to or slightly beyond the position the free end of the specimen strip will have when the package is closed for shipping. In this position the holding tab will be capable of pressing firmly against the specimen strip, with the assistance of the auxiliary end panel 55 and one or another of the side panels 14, 20. Retention of the free end edge of the specimen strip is effective in preventing endwise shifting when packaged.

FIGS. 15 through 18 show an alternate form of the invention where the retaining means for engaging the specimen strip are provided on the central base portion 11, instead of being provided on the end panel 30, as was the case in the embodiments illustrated in FIGS. 1 through 14. Common elements are shown by the same numerals in all forms of the invention shown in the drawings. A first retainer for the specimen strip is generally designated by the numeral 80 in FIG. 15 and includes two openings 81, 82 defined in the central base portion 11 of the package sheet. Both openings are of rectangular shape and are separated by a relatively narrow strip 83 which is integral with the base portion 11. The length of both openings 81, 82, as measured between the side panels 14, 20, is slightly greater than the width of the specimen strip 35, so as to hold the strip against significant lateral movement when placed in the retainer in a manner which will be explained below:

The width of openings 81, 82 measured between end panels 30, 55, differs for the two openings. Opening 81, 82 is sufficiently wide to readily accommodate the thickness of the specimen strip 35 when one end of the strip is inserted through this opening. The opening 81, however is considerably wider, approximately three times the width of opening 82. The strip 83 may be about one and half times the width of opening 82. The retainer 80 engages one end of the specimen strip 35 in a manner illustrated in FIGS. 16 and 18.

The medical specimen strips typically used for collection of biological samples taken from patients typically have a frosted surface at one end of the slide. The frosted surface allows writing on the surface by medical personnel collecting the specimen in order to identify the nature and/or source of the biological specimen on the strip 35. Typically, it is the frosted end strip 35 which is engaged to the retainer 80. The strip 35 is engaged to the retainer 80 by first inserting the end 84 into opening 81, pushing the end 84 under the strip 83 and then threading the end 84 upwardly into and through opening 82. Engagement of the strip 35 is then completed by pushing the strip 35 a short distance towards the end panel 30 until the end 84 rests on and is supported by the end support area 85 of the base portion 11 which lies between the opening 82 and the fold line 31 of end panel 30. The end 84 of the slide 35 is shown in this engaged condition in FIGS. 16 and 18. The strip 83 snugly spans the width of the strip 35 and securely retains it flat against the central base portion 11. The specimen strip 35 is held in bridging relationship across both openings 81, 82 when engaged to the first retainer 80. In this condition, the specimen strip extends across both openings between the central area of the base portion 11 and the end support area 84, underneath the retaining strip 83. Inasmuch as the length of the strip 83 is only slightly greater than the width of the specimen strip 35, the retaining strip 83 has a snug frictional hold on the strip 35 and will normally suffice to hold the specimen strip 35 against significant movement in a longitudinal direction through the retainer 80.

The specimen strip 35 is further secured in place by the end panel 30 which holds down the end 84 of the strip in the folded, packaged condition of the sheet shown in FIGS. 17 and 18. FIG. 18 shows how the strip end 84 lies close to the fold line 31 and is held between the end panel 30, which folds over the end 84 of the specimen strip, and the support area 85 under the panel 30. Consequently, the specimen strip 35 has limited if any room for longitudinal displacement towards the end panel 30, in the packaged condition of FIG. 18.

A second retainer in the form of tab 86 is defined integrally with the base portion 11 by an arcuate slit line 87 connecting the ends of two parallel slits 88. The tab 86 is connected to the central base portion at an end 89. The free end of the tap defined by the slit line 87 can be lifted from the central base portion, and an opposite end 100 of the specimen strip 35 captured under the tab 86, in a manner shown in FIGS. 16 and 18. The tab 86 tends to hold down the opposite end 100 of the specimen strip 35 against the base portion 11, and also holds the specimen strip 35 against sliding movement through the first retainer 80, under the strip 83 towards the end panel 55, as best seen in FIGS. 16 and 18. In the packaged condition shown in FIGS. 17 and 18, the end panel 55, when folded along fold line 13 bears down on the free end of the tab and assists in holding down the strip end 100 against the central base portion 11.

The side panels 14 and 20 have a combined width, in the packaged condition of the package sheet 10, which is greater than the width of the central base portion 11 between these panels. Consequently, when the flap 50 is engaged to the slit 48, as in FIG. 17, the side panels 14, 20 are forced to an arcuate configuration which is concave on the interior side of the package, so that the side flaps raised away from the specimen strip 35 supported on the base portion 11. This creates an interior space 101 above the specimen strip 35 which tends to protect and preserve the biological specimen carried on the specimen strip. The end flaps 30, 55 contribute in supporting the side flaps 14, 20 in this arcuate configuration by pushing up on the underside of the side flaps in the packaged condition of the sheet 10.

It must be understood that the specimen strip retainer 80 can be positioned at different locations on the sheet 10 in addition to the two positions illustrated in the drawings, i.e on the end flap 30 and on the central base portion 11 adjacent to the end flap 30. Also, the first specimen strip retainer 80 may be used with or without the second retainer or tab 86.

DETAILED DESCRIPTION OF THE PREFERRED EMBODIMENTS

FIGS. 19 through 27 show yet another form of the invention wherein the slide retainer has been modified and consists of two U-shaped cuts or slits in the central base portion 11 of the package sheet 100, instead of two rectangular openings as provided in previously described forms of the package. Another feature of this embodiment consists of end panels modified to provide positive support for the side panels in the packaged condition of the sheet 100, so as to better resist exterior force tending to flatten the various panels against the contents of the package and particularly against the specimen slide, both to protect the relatively fragile glass slide against breakage and to safeguard the biological specimen on the slide against contact with the packaging material. Common elements in all forms of the invention are shown by the same numerals, which in the case of modified elements in the new embodiment are designated by the same numeral primed.

With reference to FIGS. 20 and 21 of the drawings, a sheet of packaging material for assembly into a specimen package is indicated generally by the reference character 100, and consists essentially of a single sheet of package material specially cut for folding in a distinctive fashion. The package is made up of two central base portions 11 and 12 separated by a transverse fold line 13. The two base portions together form, in effect, a long rectangular bottom for the package in its initial or original form.

On one side of the base portion 11 is a side panel 14 with a captive side edge joined by a fold line 15 to a corresponding side edge of the base panel 11, leaving a free edge 16. Similarly, for the base portion 12 there is a side panel 18 with a captive side edge joined along a fold line 19 to a corresponding side edge of the base portion 12. The fold lines 15 and 19 are continuous with respect to each other forming one fold line for the combined side panels 14 and 18, permitting them to be folded over the initially joined base portions 11 and 12.

On the opposite side of the base portion 11 is a side panel 20 having a captive edge joined to a corresponding edge of the base portion 11 along a fold line 21. Again, for the base portion 12 there is a side panel 22 joined along a fold line 23 to a corresponding edge of the base portion 12. The combined width of the side panels 14 and 20 is materially greater than the width of the corresponding base portion 11. Similarly, the combined width of the side panels 18 and 22 is materially greater than the width of the base panel 12.

At the free end of the base portion 12 is an end panel 26 joined at its captive edge to a corresponding edge of the base panel 12 along a fold line 27. The fold line 27 is in alignment with an end edge 28 of the side panel 18 and a similar end edge 29 of the side panel 22.

At the opposite end of the package there is another end panel 30' joined at its captive edge to a corresponding edge of the base portion 11 along a fold line 31. The fold line 31 is in alignment with an end edge 32 of the side panel 14 and a corresponding end edge 33 of the side panel 20.

The side panels 14, 20 are attached to side panels 22, 18 respectively by lines of perforations 59, 58 respectively. The tear lines 58, 59 are in line with the fold line 13 between the central base portions 11 and 12. An auxiliary end panel 55' is defined by corner cut lines 100 and 102 joined by a line of perforations 104. The end panel 55' is joined to the central base portion 11 by fold line 13.

Each of the three end panels 26', 30' and 55' on the package sheet 100 has two side edges 106, 108 connected by a free edge 110. The three end panels are characterized in that the side edges in each panel diverge from each other towards the free edge of the panel, such that each end panel has a trapezoidal shape in which the free edge 110 is longer than the captive edge attached to the corresponding central base portion by the fold line common to the end panel and the central base portion.

In addition, each end panel has two fold lines 112, 114 diagonal to both the free edge 110 and a corresponding side edge 106, 108, so as to define triangular corner portions 116 118 of the end panel. Although numerals 106-114 are shown only for end panel 26' in FIG. 21, it will be understood that all three end panels are similar.

Side panels 20, 22 are each divided by a longitudinal fold line 120 parallel to the fold lines 21, 23 into inner panels 20', 22' and outer panels 20", 22". Likewise, panels 14 and 18 are divided by longitudinal fold line 122 into inner panels 14', 18' and outer panels 14" and 18".

In FIG. 22 a slide bearing package sheet portion 100' has been separated from the initial package sheet 100 by tearing along perforation lines 58, 59 and 104, resulting in a final package sheet 100' consisting of the central base portion 11, end panels 30' and 55', and side panels 14, 20. The original sheet 100 is folded to make an initial package shown in FIGS. 19 and 27, in which end panel 26' cooperates with end panel 30' to support the side flaps 20/22 and 14/18 in a manner analogous to that described for the final package of FIG. 24. The side flaps 18 and 22 each break along fold lines 122, 120 respectively, such that their inner panels 18', 22' are supported on the corners portions 118, 116 of end panel 26', while the outer panels 18" and 22" lie substantially flat on the central edge portion 110' of end panel 26', which elevated above the central base portion 12 and supported on the bent corner portions 116, 118 of the end panel, all as described in connection with end panels 55' and 30'. The initial package of FIG. 19 contains the various specimen collecting implements including scraper 47, swab 46 and brush 46', which may be loosely placed within the package. These implements are discarded once the biological or medical specimen has been collected and deposited on the specimen slide 35. The slide bearing portion 100' of the package sheet 100 is then separated from the original sheet and folded as described and shown in FIGS. 22-24, to make the final package which is transported to the specimen analysis site.

The sheet 100' is folded to make a final slide specimen package as shown in the sequence of FIGS. 22 through 24. The corner portions 116, 118 of each end panel 30', 55' are bent upwardly along lines 112 to a shallow angle relative to the central portion 124 of each end panel The end panels 30', 55' are then folded along lines 31, 13 respectively over the central base portion 11 to a position illustrated in FIG. 23, in which the side edges 106, 108 of the two end panels are congruent with fold lines 21, 15 respectively. The initially divergent side edges 106, 108 are now mutually parallel and the free edge 110 now has a central portion 110' which lies above and parallel to the central base portion 11, and two end edge portions 110" which slope down from the central portion 110' to the plane of the central base portion 11. As shown in FIG. 23, the central portion 124 of each end panel is now supported by the corner portions 116, 118 in an inclined condition away from contact with the medical slide 35 on the base portion 11. The central portion 124 rises from the fold line 13 to the elevated free edge portion 110'. The height of the edge portion 110' above the central base portion 11 is related to the angle of divergence between the side edges 106, 108 of the end panel. The greater this angle, the higher the position of the edge portion 110'. In this condition of the package, the corner portions 116, 118 rise from the fold lines 21, 15 respectively, to the level of the edge portion 110' and the corner portions lie at an angle both to the base portion 11 and to the central portion 124 of the end panel.

The slide bearing sheet portion 110' is then folded to its final, fully packaged condition shown in FIG. 24, by folding first the side flap 14 over the two folded end panels 30', 55'. The spacing between fold lines 15 and 122, which determines the width of the inner panel 14' is equal to the length of an end edge segment 110" of the two end panels. The side panel 14 breaks along the fold line 122 such that the inner panel 14' lies flat against and parallel to the plane of the two corner portions 118 of the opposite end panels 30', 55'. The outer panel 14" lies parallel to the central base portion 11 and is supported on the horizontal elevated edge portions 110' of the two end panels.

The final package of FIG. 24 is completed by folding of side flap 20, in which the inner panel 20' is supported against and parallel to the plane of the two corner portions 116 of the end panels 30' and 55'. Side panel 20 breaks along fold line 120 such that the outer panel 20" lies horizontally flat against on outer panel 14" of the opposite side panel 14, and the outer panel 20" is also supported on the horizontal elevated edge portions 110' of the end panels, in parallel relationship to the central base portion 11. Flap 50 is engaged to the retaining slit 48 to secure all side panels and end panels in the final packaged condition of FIG. 24.

It must be appreciated that in this final packaged condition the side edges 106 and 108 of the end panels are captive between the corresponding inner panel 14', 20' and the base portion 11. The side edges 106, 108 of each end panel cannot spread apart because of this captive condition. This confers considerable weight bearing support to the central portion 124, and consequently to the raised edge 110' of the end panels, which thus resist a force tending to press either the end panels or the side panels against the specimen bearing upper surface of the medical slide 35. The medical specimen on slide 35 is therefore better protected against the tendency to squeeze the top and bottom of the package during handling, or against the weight of other articles during transport from the specimen collecting site to the specimen testing site.

Another modification to the package sheet 100 over previously described embodiments relates to the slide retainer which is generally designated by the numeral 130 on the first central base portion 11 in FIGS. 20-22. The first slide retainer 130 has two U-shaped cuts 132, 134. Cut 132 has a central portion 136 perpendicular to the side fold lines 15, 21, and two end portions 138 which are mutually divergent in a direction away from the central portion 136 and towards end panel 30'. The other U-shaped cut 134 likewise has a central portion 140 and two end portions 142 which are mutually parallel and perpendicular to the central portion 140, and extend in the opposite direction from the end portions 138, away from the U-cut 132, as best seen in FIG. 21a. The central portions 136, 140 of the two U-cuts 132, 134 respectively, are mutually parallel and spaced apart to define between them a slide retaining band 144 which is integral with the central base portion 11 of the sheet 100.

The two U-cuts 132, 134 of the first slide retainer 130 in effect define two tabs 152, 154 respectively which are oriented towards each other on either side of the retaining band 144. A medical specimen slide 35 is engaged to the first slide retainer 130 by pressing down on the tab 154 until the tab bends down and separates from the retaining band 144 to create an elongated opening in the central base portion 11. The end of the slide is pushed into this opening and the opposite tab 152 may then be pressed down and similarly separated from the retaining band 144 to make a second elongated opening in the central base portion 11 on the other side of the band 144, until the slide end can pass through beneath the retaining band 144 and onto the tab 152. The slide 35 is then pushed through the retainer 130 under the band 144 until the same end of the slide reaches the second slide retainer 150, where end 148 of the tab retainer 150 is lifted and the slide end advanced under the tab retainer 150, which may then be pressed down over the slide end. FIGS. 20, 22 and 25-27 show the specimen slide 35 installed in engagement with both slide retainers 130 and 150. The slide remains engaged to the sheet 100 as in FIG. 20 through the specimen collection procedure, and is normally not removed from the package sheet 100 or 100' until it is received at the specimen analysis site.

A second slide retainer, generally designated by numeral 150, is defined by a third U-shaped cut 146 forms a tab which has a free end 148 extending towards the first slide retainer 130, as best shown in FIGS. 21, 21a and 22. The first slide retainer 130 is proximal to first end panel 30', while the second slide retainer 150 is proximal to the second end panel 55'. The first slide retainer receives one end of slide 35 while the second slide retainer 150 engages an opposite end of the slide which remains free of the first slide retainer 130. Both ends of the specimen slide are consequently secured to the central base portion 11 by the two slide retainers, as best seen in FIGS. 20, 26 and 27 in both the initial and final packaged forms of the sheet 100. The arrangement of the two slide retainers on the central base portion 11 is such that the specimen slide 35 is held against significant longitudinal movement between the first end panel 30' and the second slide retainer 150. In the final packaged condition of FIGS. 24-26, the tab retainer 150 is held down against the specimen slide 35 by the second end panel 55', as best seen in FIG. 26, to secure the retentive engagement of the slide at that end.

While particular embodiments of the present invention have been shown and described, it will be obvious to those skilled in the art that changes and modifications may be made without departing from the invention in its broader aspects and, therefore, the aim of its attendant claims is to cover all such changes and modifications as fall within the true spirit and scope of this invention.

Having described the invention, what is claimed as new in support of Letters Patent is as follows:

1. A specimen package for containment of a medical specimen slide, said package comprising:

a sheet of package material having a base portion, panel means joined to said base portion, and latching means for holding said panel means in a packaged condition;

slide retaining means in said base portion, said retaining means comprising two cuts, said cuts each having a central portion intermediate opposite end portions of the cut, said central portions of said cuts being spaced apart to define a retaining band integral with said base portion, said end portions of one of said cuts being oriented away from said end portions of the other of said cuts to define two tabs having free ends extending towards each other and separated by said retaining band, said tabs yielding to admit a medical specimen slide on said base portion under said retaining band.

2. The package of claim 1, wherein said opposite end portions in each of said cuts are substantially parallel to each other.

3. The package of claim 1 wherein said end portions of one of said cuts are mutually parallel and said end portions of the other of said cuts are mutually divergent.

4. The package of claim 1 wherein said end portions of each of said cuts are equal or greater in length than the width of said retaining band measured between said central portions of said cuts.

5. The package of claim 1 wherein said panel means comprise a first end panel and a second end panel at opposite ends of said base portion, said first slide retaining means being proximal to said first end panel for engaging a medical specimen slide near one end thereof, and further comprising a third cut defining second slide retaining means proximal to said second end panel for engaging a medical specimen slide at an opposite end thereof.

6. The package of claim 5 wherein said second slide retaining means are positioned so as to hold a medical specimen slide against significant longitudinal movement between said first end panel and said second slide retaining means.

7. The package of claim 5 wherein said second slide retaining means is a tab having a free end extending towards said first slide retaining means.

8. The package of claim 7 wherein said tab is held against said slide by said second end panel in said packaged condition.

9. A specimen package assembly for containment of a specimen strip, said package assembly comprising:

a sheet of package material having a base portion, a plurality of side panels and end panels joined to said base portion, and latching means for holding all said panels in packaged condition; and retaining means on said sheet for holding a specimen strip to said base portion;

each end panel having two side edges extending from said base portion to a free edge of said end panel, two corner portions each corner portion being defined by a respective fold line diagonal to both said side edges and said free edge and a central portion defined between said corner portions and between said free edge and a first fold line joining said end panel to said base portion, each corner portion being foldable along its diagonal fold line for placing the length of said side edges against second fold lines joining said side panels to said base portion such that said corner portions are supported by said side panels against spreading apart and flattening onto said base and said center portion and side panels are supported away from contacted with a specimen strip held to said base portion in said packaged condition.

10. The package of claim 9 wherein each said free edge has a width greater than the width of said base portion between said side panels.

11. The package of claim 9 wherein said side edges diverge from each other towards said free edge on each said end panel and said free edge has a width greater than said base portion between said side panels.

12. The package of claim 9 wherein said end panels are trapezoidally shaped with a shorter edge attached along a first fold line to said base portion, said free edge being opposite to and wider than said shorter edge.

13. The package of claim 9 wherein said side panels each have a side panel fold line in common with said base portion, and said side edges are congruent with said side panel fold lines and captive between said side panels and said base portion in said packaged condition for supporting said corner portions in said transverse condition, thereby to keep said end panels from contact with a specimen slide held to said base portion by said retaining means.

14. The package of claim 13 wherein each of said side panels is divided by a fold line into an inner panel and an outer panel, such that in said packaged condition the inner panels are supported flat against said corner portions and said outer panels are supported on a free edge of said central portions of the end panels in a plane parallel to said base portion.

15. A specimen package assembly for containment of a specimen strip, said package assembly comprising:

a sheet of package material having a base portion, a plurality of side panels and end panels joined to said base portion, each said side panel having a first fold line in common with said base portion, each side panel divided by a second fold line into an inner panel and an outer panel, and latching means for holding all said panels in packaged condition;

retaining means integral with said sheet for holding a specimen strip to said base portion;

each end panel having a free edge between two side edges, and two corner portions each defined by a respective third fold line diagonal to an adjacent side edge and said free edge, said corner portions being foldable to a condition transverse to both said base portion and a central portion of said end panel in said packaged condition, said central portion extending from said free edge to said base portion, such that in said packaged condition each of said side edges on each said end panel is in longitudinal contact with one of said first fold lines and supported by said side panels against flattening onto said base under pressure applied to said central portion, such that said inner panels lie against said corner portions and said outer panels are supported on a free edge of each of said central portions of the end panels in a plane parallel to said base portion.

16. A specimen package for containment of a medical specimen slide, said package comprising:

a sheet of package material having a first central base portion, first and second end panels at opposite ends of said first central base portion, and first and second side panels joined along fold lines to said first central base portion; a second central base portion joined to one of said ends by tear lines, a third end panel connected to a free end of said second central base portion, third and fourth side panels joined to said second central base portion along fold lines and also connected to said first and second side panels respectively along said tear lines, and latching means for holding said side panel to said central base portions in a packaged condition;

first retaining means for holding a specimen slide to said base portion, said retaining means comprising two U-shaped cuts, said cuts each having a central portion intermediate opposite end portions of the cut, said central portions of said cuts being mutually parallel and spaced apart to define a retaining band integral with said base portion, end portions of one of said U-shaped cuts extending away from said end portions of the other of said U-shaped cuts to define two tabs having free ends extending towards each other and separated by said retaining band, said tabs yielding to admit a medical specimen slide on said base portion under said retaining band.

17. The package of claim 16 wherein said end portions of one said U-shaped cut are mutually parallel and said end portions of the other of said cuts are mutually divergent.

18. The package of claim 16 wherein said end portions of each of said U-shaped cuts are equal or greater in length than the width of said retaining band measured between said central portions of said cuts.

19. The package of claim 16 said first retaining means being proximal to said first end panel, and further comprising a third cut defining second retaining means proximal to said second end panel for engaging a slide at an end free of said first slide retaining means.

20. The package of claim 19 wherein said second slide retaining means is a tab having a free end extending towards said first slide retaining means.

21. The package of claim 20 wherein said tab is held against a slide by said second end panel in a detached and packaged condition of said first central base portion.

22. The package of claim 16 wherein each of said end panels have a free edge and a second fold line diagonal to said side edge and free edges for dividing said end panel into a central portion and two corner portions, said corner portions being foldable to a condition transverse to both said base portion and said central portion in said packaged condition, said side edges of the end panels being supported between said side panels and a corresponding one of said central base portions against displacement by force applied to said central portion of the end panel, thereby to keep said central portion from contact with a specimen slide retained to said central base portion.

23. The package of claim 22 wherein each of said side panels is attached along a third fold line to a corresponding one of said central base portions and is divided by a fourth fold line into an inner panel and an outer panel, the inner panels lying against said corner portions and said outer panels being supported on a free edge of said central portion of the end panels in said packaged condition.

24. The package of claim 16 further comprising third retainer means for retaining specimen collection implements to said second central base portion, said third retainer means comprising two U-shaped cuts, said cuts each having a central portion intermediate opposite end portions of the cut, said central portions of said cuts being mutually parallel and spaced apart to define a retaining band integral with said base portion, end portions of one of said U-shaped cuts extending away from said end portions of the other of said U-shaped cuts to define two tabs having free ends extending towards each other and separated by said retaining band, said tabs yielding to admit specimen collection implements on said base portion under said retaining band.

25. A specimen package for containment of a medical specimen slide, said package comprising:

a sheet of package material foldable to a packaged condition;

two cuts in said sheet, said cuts each having a central portion intermediate opposite end portions of the cut, said central portions of said cuts being mutually parallel and spaced apart to define a retaining band integral with said sheet, said end portions of one of said cuts being oriented away from said end portions of the other of said cuts to define two tabs having free ends extending towards each other and separated by said retaining band, said tabs yielding to admit a medical specimen slide against said sheet under said retaining band.

* * * * *